United States Patent [19]

Scheicher et al.

[11] Patent Number: 4,525,145
[45] Date of Patent: Jun. 25, 1985

[54] CONNECTING DEVICE FOR JOINING A SUPERSTRUCTURE ELEMENT WITH AN IMPLANT MEMBER

[75] Inventors: Hans Scheicher, Rondell Neuwittelsbach 4, 8000 Munich 19; Dieter Siegele, Freiburg; Uwe Soltesz, Merzhausen, all of Fed. Rep. of Germany

[73] Assignees: Fraunhofer-Gesellschaft zur Forderung der angwandten Forschung e.V., Freiburg; Hans Scheicher, Munich, both of Fed. Rep. of Germany

[21] Appl. No.: 496,630

[22] Filed: May 20, 1983

[51] Int. Cl.³ ............................................. A61C 8/00
[52] U.S. Cl. ................................................... 433/173
[58] Field of Search ................ 433/173, 174, 175, 176

[56] References Cited

U.S. PATENT DOCUMENTS

| 3,589,011 | 6/1971 | Sneer | 433/174 |
| 3,618,212 | 11/1971 | Weissman | 433/174 |
| 3,708,883 | 1/1973 | Flander | 433/174 |
| 3,934,347 | 1/1976 | Lash et al. | 433/180 |
| 4,318,696 | 3/1982 | Kasama et al. | 433/173 |

FOREIGN PATENT DOCUMENTS

| 15599 | 9/1980 | European Pat. Off. | 433/173 |
| 923383 | 2/1955 | Fed. Rep. of Germany | 128/62 A |
| 2015324 | 11/1971 | Fed. Rep. of Germany | 3/1.9 |
| 2249051 | 4/1973 | Fed. Rep. of Germany | 433/173 |
| 2413883 | 9/1975 | Fed. Rep. of Germany | 433/173 |
| 2704390 | 8/1978 | Fed. Rep. of Germany | 433/173 |
| 2824214 | 12/1979 | Fed. Rep. of Germany | 433/173 |
| 2830025 | 1/1980 | Fed. Rep. of Germany | 433/173 |
| 2905647 | 8/1980 | Fed. Rep. of Germany | 433/173 |
| 237877 | 9/1945 | Switzerland | 433/173 |

Primary Examiner—John J. Wilson
Attorney, Agent, or Firm—Walter H. Schneider

[57] ABSTRACT

A connecting device is disclosed for operatively interconnecting a superstructure element and an implant member having at least one bore, which device includes a rod member made of a material of construction having a high modulus of elasticity and which device further includes a projection means made of the same material of construction as used for the rod member, or a dissimilar material, and the device further including, as required, an envelope means. There are further disclosed an implant member which includes the aforesaid connecting device, and a method for arranging the connecting device in an implant member.

11 Claims, 10 Drawing Figures

CONNECTING DEVICE FOR JOINING A SUPERSTRUCTURE ELEMENT WITH AN IMPLANT MEMBER

BACKGROUND OF THE INVENTION

1. Field of the Invention

The present invention relates generally to improvements in or relating to connecting devices for use with components such as dental implants, or implants for artificial joint reconstructions. More particularly, the present invention is concerned with a connecting device for joining an implant or implant member, which implant member includes a bore, and a superstructure element. The invention is also concerned with an implant member which is adapted to receive the connecting device, as well as with a method of arranging the connecting device in the implant member.

The connecting device or element in accordance with the present invention is particularly suitable for implants intended for roots of teeth, however, such a connecting device is also suitable for implants associated with artificial joint reconstructions.

The connecting device for implants in accordance with the present invention is particularly adapted to distribute an introduced force, or forces, from the point of force introduction, for example, the artificial tooth or a superstructure, into the implant base, for example, the jaw bone, particularly in such a manner that localized overloading or excessive stressing of the bone is substantially prevented.

In the case of many endo-osseous implants (artificial alloplastic tooth root anchored in the bone) there often arises, after brief to periods to several years of wearing of an implant, a bone reduction at the implant base, which ultimately leads to the loss of the implant or even its fracturing.

This so-called 'resorption' of the bone can be attributed only in part to insufficient biocompatibility (compatibility with the tissue) of the implant member material, or to infections. A material cause of the bone reduction, however, is due to biomechanical stressing of the implant base. Thus, a localized, frequently repeated, loading or stressing of the bone, with mechanical stress peaks, leads to the bone reduction. This applies to dental root implants as well as to bone or joint implants. During the implanting of such implant members it is, accordingly, of determining importance for a lasting existence thereof in the organism, that such damaging stress peaks will be prevented by means of suitable load distributing mechanisms.

In the case of implants for the replacement of tooth roots, as in the case of other types of implants, there arise a number of load situations which, in the case of direct frictional connection between the load which is introduced and the implant base, bearing or socket, via a rigidly situated implant, lead to such localized stress peaks and, thus, to resorption, loosening and loss of the implant.

The natural tooth is supported by an elastic fiber network, the periodontium, in a manner similar to being supported in a hammock and is there joined to the surrounding bone. By means of this mechanism the tooth can be elastically deflected when subjected either to horizontal or vertical forces, whereby the bone bearing or base is predominantly subjected, via the fibers, probably largely uniformly, to tensile stressing. Thus, the physiological deflection of an upper incisor, for example, on being subjected to a horizontal force of 5 N, is approximately 20 to 80 $\mu$m. On being subjected to an equal, but vertically directed force, the root of the tooth is pressed into the base by approximately 20 to 30 $\mu$m. Simultaneously there occurs, by way of mechanoreceptors in the periodontium, via cortical and subcortical control mechanisms (cerebral nerves), a coordination and limiting of the force-release of the muscles employed for chewing.

In the case of an endo-osseous implant such dental sensorium is not present and, thus, there is also not present a control of the force introduction, such that this alone may lead to overloading. Furthermore, an implant is generally form-lockingly surrounded by bone growth, or possibly even force-lockingly surrounded by bone growth. In the case of a rigid connection between the implant and the replacement of a tooth, or a bridge, the entire force applied is transmitted directly, and locally limited, via the implant, into the implant base, bearing or socket. In the case of a natural tooth, in contrast, when a point-like introduction of a load occurs, there follows, initially, a deflection, or sinking-in, respectively, of the tooth and, at a significant relation of the rows of teeth and the teeth ridges with respect to one another, very rapidly a support, or dissipation, of the chewing forces by the other teeth. This prevents an overloading of individual tooth holding apparatus. In the case of form-lockingly and force-lockingly ingrown implants this deflection possibility does not exist, and stress increases arise in the bone base and, thus, bone reduction and loss of the implant.

By way of photoelastic investigations and numerical calculations it was determined that primarily the horizontal components of the forces applied at the tooth lead to considerable load or pressure peaks, particularly at the exit edge of the implant from the bone, at the so-called 'corticalis' (cortical bone). This provides an explanation for the repeatedly observed conical opening and regeneration of the bone around the implant.

In the case of a vertical loading, the forces are largely introduced symmetrically via the wall of the implant and into the bone, via the bottom of the implant. Normally in such a case localized stress peaks will not occur, however, a general overloading of the entire implant bed can also occur, since the implant is rigidly connected, in contrast to a natural tooth, to the bone.

In the FIGS. 1 to 4 there are graphically presented the results of calculations using a model (finite-element calculations), which were carried out at the Fraunhofer-Institut für Werkstoffmechanik (Fraunhofer Institute for Materials Mechanics) at Freiburg.

Figure 1:
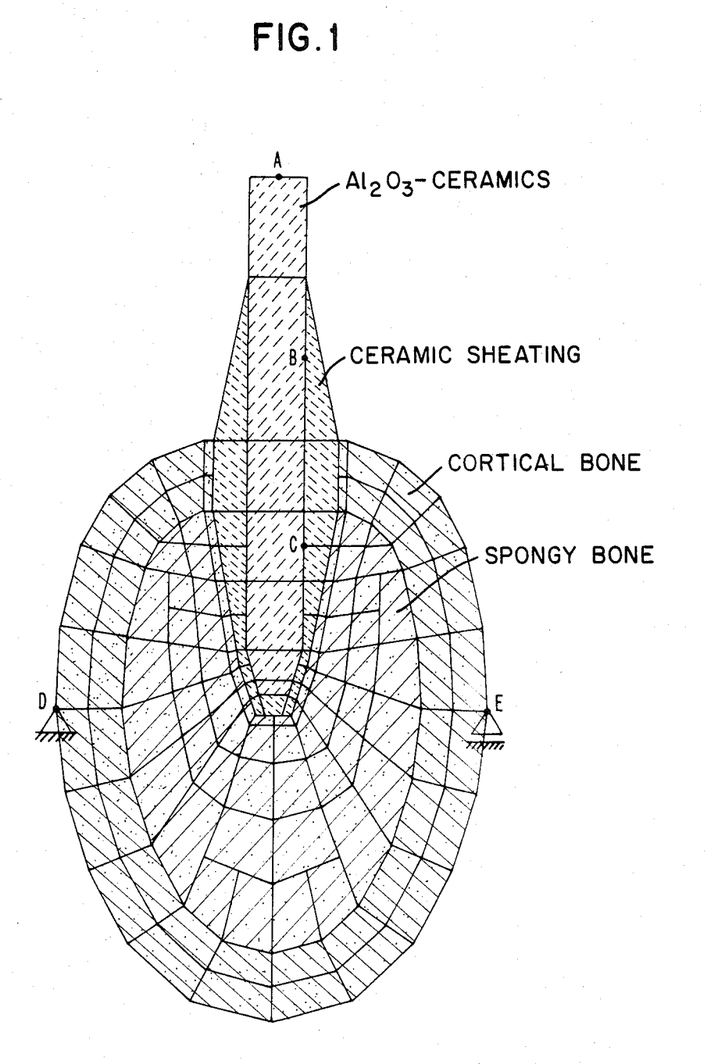
FIG. 1 is a schematical representation of a model for finite-element calculations, with the jaw and the implant being shown in cross section.

FIG. 1 shows a schematic representation of the finite element model (FE-model) of an implant in the lower jaw, assuming a steady connection between the implant and the bone base, or bearing or socket.

There is shown a cross section through the jaw and the implant. The bone is nonhomogeneous and is comprised of a hard corticalis-shell and the soft inner spongiosa. The modulus of elasticity (E-modulus) of the corticalis is assumed to be 20,000 N/mm$^2$, that of the spongiosa 2,000 N/mm$^2$, and that of the implant (Al$_2$O$_3$-ceramic) 380,000 N/mm$^2$.

Figure 2:
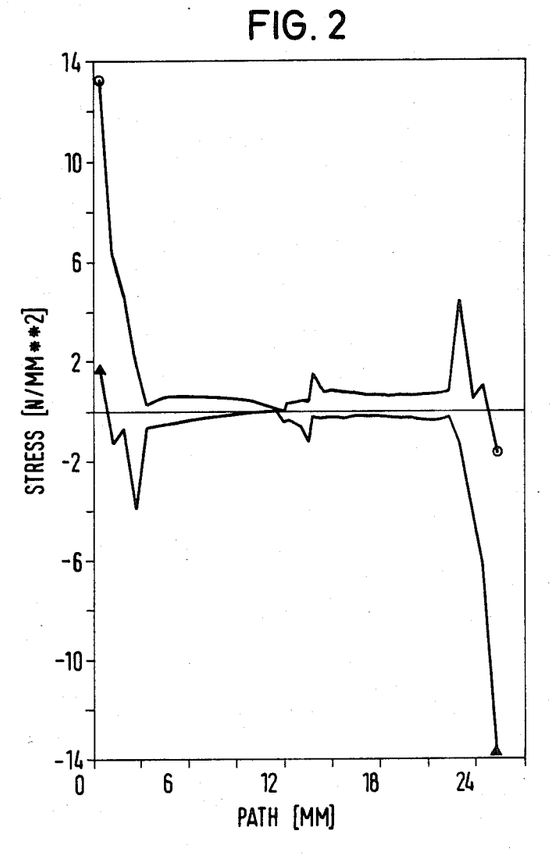
FIGS. 2 to 4 are diagrams showing pressure per unit area as a function of distance.

FIG. 2 shows the distribution of the primary tensions in the bone along the boundary surface of the implant, whereby the abscissa describes the path along the surface of the implant in counter-clockwise direction. As the load there is assumed a strictly horizontally directed force of 10 N, which is applied at the point A (see FIG. 1), approximately at the level of the cutting edge of a front tooth. The curve clearly indicates the stress peaks which are generated in the corticalis.

Figure 3:
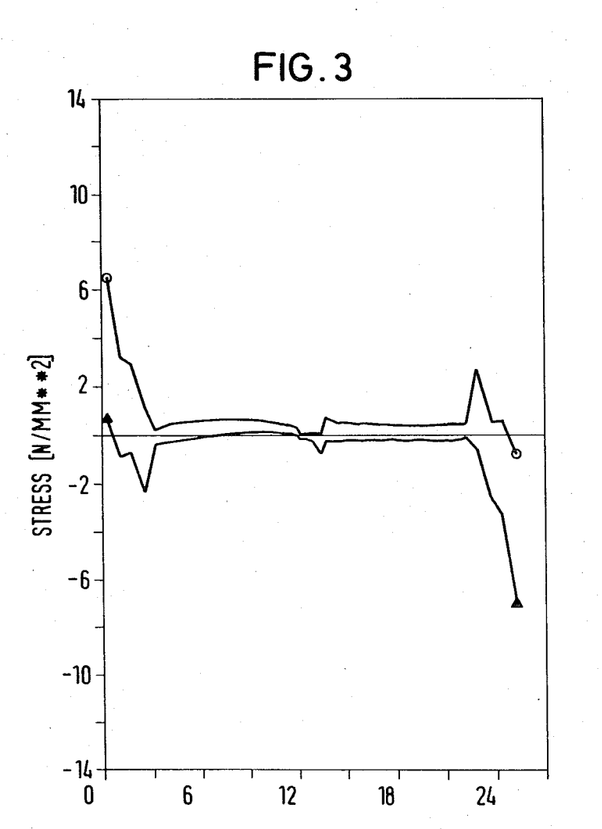
Figure 4:
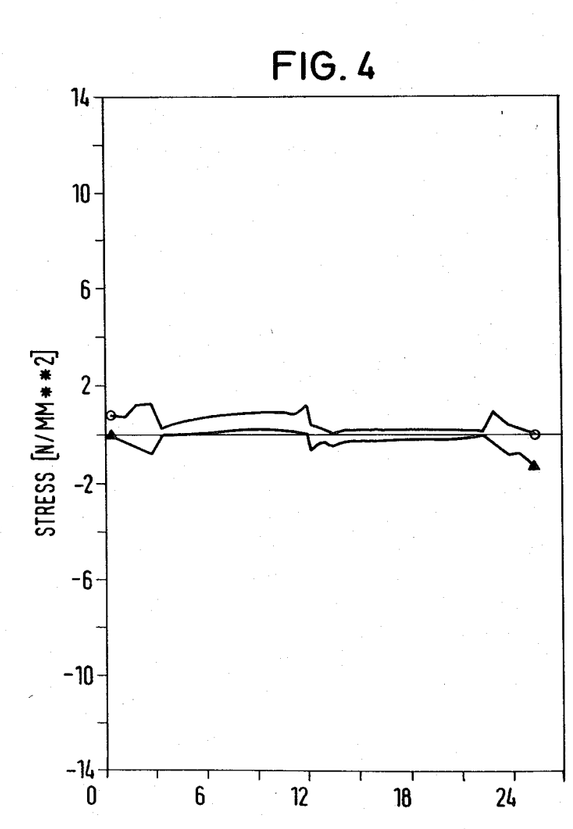

FIGS. 3 and 4 show the distribution of stress for the case where the introduction of the horizontal force is not at point A (see FIG. 1), but at point B, or C, respectively, which corresponds approximately to the center of rotation of the implant.

A comparison of FIGS. 2 to 4 clearly indicates that the stress peaks, which occur at the transitional edge of the implant into the bone, are dependent upon the location of force introduction, i.e., the torque which is introduced. For example, if the force is applied near the center of rotation, then the stresses of the bone can be nearly completely eliminated at the transitional exit edge of the bone (FIG. 4).

2. Description of the Prior Art

Proposals to reduce, or avoid, the non-physiological pressure peaks in the bone bed are known. These are primarily based on the concept—physically arguable—of reduction of the pressure peaks by means of force-absorbing, or shock-absorbing, respectively, intermediates or buffers, which exhibit an 'elastic' behavior (i.e., presumably exhibit a reduced rigidity). These buffers are comprised either of an attachment to the implant, which attachment extends into the superstructure (DE-OS No. 2 704 390, DE-OS No. 2 824 214, DE-OS No. 2 413 883, DE-OS No. 2 950 219, DE-OS No. 2 830 025; DE-OS=German Offenlegungsschrift), and/or are comprised of a pin (DE-OS No. 2 824 214), or an intermediate layer within the implant part embedded in the bone (DE-OS No. 2 413 883, U.S. Pat. No. 3,934,347). These are all made of a soft plastic or synthetic material. All such designs have only a limited effect in the redistribution of the pressure or force and, thus, in the reduction of the pressure peaks. This is due thereto that there is allowed, because of a somewhat increased mobility of the superstructure, primarily in vertical direction and with a suitable arrangement, a limited distribution of the introduced force to the neighboring teeth, or further columns of the superstructure. The danger of the horizontal force component, however, is not, or only insignificantly, reduced, since the point of force introduction remains constant, or is only slightly relocated. Thus, the known devices can not help to prevent the bone reduction. This also applies in the case of the proposals described in DE-OS No. 2 015 324, DE-PS No. 923 383 (DE-PS=German Patent) and U.S. Pat. No. 3,934,347. A redistribution of the introduced horizontal components could firstly be achieved by the special arrangement comprising a rod with a projection means and the support thereof in a suitable envelope.

SUMMARY OF THE INVENTION

There has continued to remain, therefore, a need for enhancing the benefits derived from implants.

It is accordingly an object of the present invention to provide a connecting device for an implant with which the pressure peaks at the exit interface of implant and bone are reduced, or substantially prevented, whereby there will be reduced, or prevented, respectively, the danger of bone reduction at this location and whereby the disadvantages of the known devices are substantially eliminated.

In accordance with the present invention this is achieved thereby that the introduced forces, directed perpendicular with respect to the main axis of the implant, against the superstructure, are redirected into the interior of the implant, in order to achieve a uniform distribution of the stresses arising due to the bone implant in the bone base. In accordance with the present invention there is provided a connecting device for joining an implant member to a superstructure, with said body including a bore which comprises a rod member of a material of construction having a high modulus of elasticity, and a projection means which is of a material of construction which is the same as, or dissimilar to, the material of construction of the rod member.

In accordance with a preferred embodiment of the invention the connecting device includes an envelope means for enclosing the device, which envelope means corresponds in shape to that of the bore of the implant member, and which envelope means is adapted to surround the rod member together with the projection means. The envelope means is made of a material which has the same modulus of elasticity as the material of which the rod member is made, or has a lower modulus of elasticity than the rod member material.

The present invention is further concerned with an implant member which includes the claimed connecting device.

Further embodiments of the invention and other inventive features are contained in the claims.

DESCRIPTION OF THE DRAWINGS

In the drawings, in which FIGS. 5 to 10 illustrate that which is presently regarded as the best mode of carrying out the invention.

DESCRIPTION OF THE PREFERRED EMBODIMENTS

Figure 5:
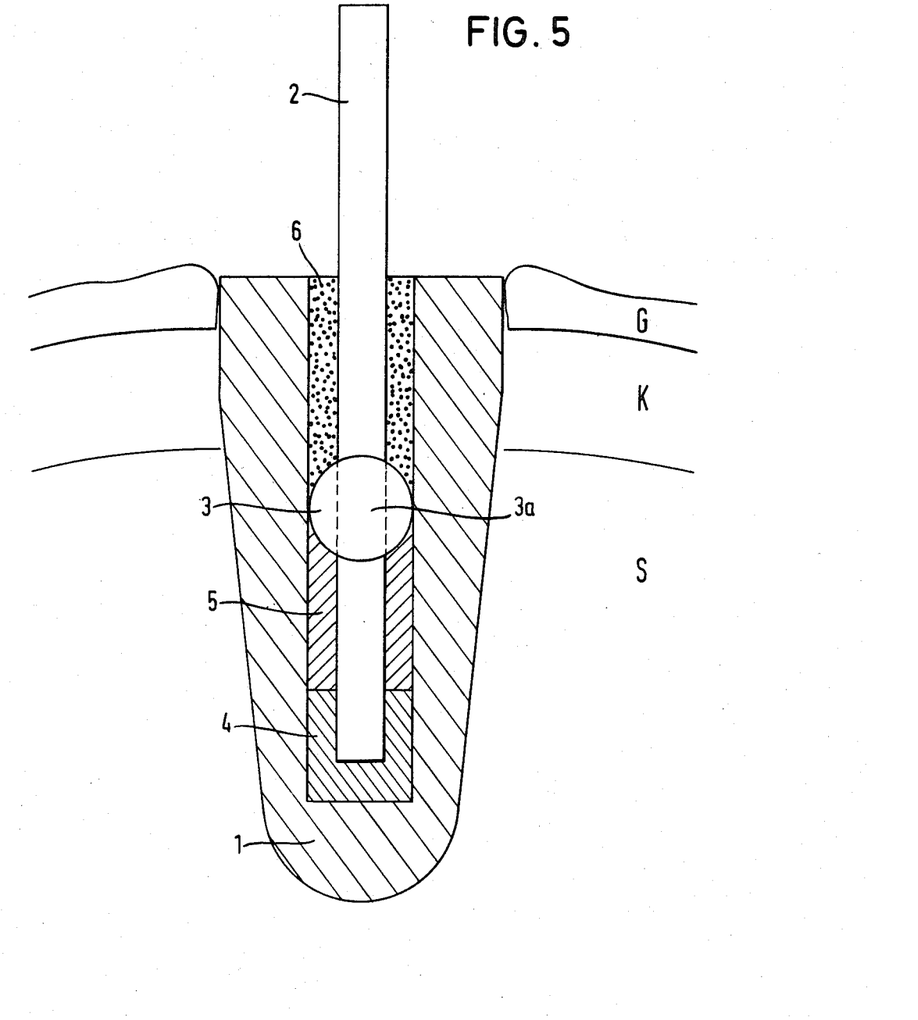
FIG. 5 is a cross-sectional view of a connecting device in accordance with one embodiment of the invention.

In FIG. 5 there is shown in the most general configuration a connecting device in accordance with the present invention. Numeral 1 designates the implant, or implant member. The implant member can generally be made of any biocompatible (tissue-compatible) material, or of a material which is bioactive (tissue-active), which material will have the required mechanical stability. The implant member can have any desired outer configuration. The implant member is shown to be located in a jaw, with the outer, hard, bone shell K (corticalis), the inner, soft, bone substance S (spongiosa) and the gum G (gingiva). However, the implant can be arranged in any other bone structure.

The implant member has an interior bore for receiving therein the connecting device. The implant member bore may be furnished with an internal thread.

The connecting device includes a rod member, designated by the numeral 2, of a material with high rigidity, i.e., with a high modulus of elasticity. Examples of such materials include metals such as surgical steels, cobalt-chromium base alloys, noble metal alloys, ceramic materials, or composite materials, such as, for example, carbon-fiber reinforced carbon materials, or synthetic or plastic materials. Preferred materials for the rod member 2 are the aforementioned metals.

The rod member 2 may furthermore be made of a homogeneous material, or of a nonhomogeneous composite material, such that along the axis thereof the modulus of elasticity will vary. It is preferred that the rod member 2 is of a homogeneous material.

The rod member 2 may have a cross section which is round, oval, multi-cornered, or any other desired cross section. It is preferred, however, that the cross section is round. The rod member 2 may have a constant diameter, or the diameter may vary continuously or discontinuously, along the longitudinal axis thereof.

In accordance with a preferred embodiment of the present invention, the rod member 2 is furnished in part, or fully, over its length, with an external thread. Preferred is a rod member with an external thread over its entire length, so that one, after introducing the rod member into the implant and the implant has been placed in the bone, can thread, onto the rod member portion extending from the implant, the artificial tooth, or respectively, the joint reconstruction component.

By shortening its upper and lower ends, the rod member 2 can be adapted as desired to the pertaining length of the implant. The rod member, with a projection means 3, to be described in detail below, is adapted with its length to the implant by shortening the rod, such that the projection 3 is located approximately 0 to 40% above the middle in the bone-embedded part of the implant, in special cases also below the middle. The precise location will be determined by the type of superstructure and the location of the implant.

As is indicated above, the rod member 2 includes a appropriate increase in diameter, or similar projection or projection means, for operatively joining the rod 2 to the implant 1. The projection 3 can be of a material having the same modulus of elasticity as the rod 2, or the material may be such that the modulus of elasticity would be different as that of the rod material. The projection can be made, for example, of the same metals, ceramic or composite materials as the rod member 2, or it can be made of plastic or synthetic materials. Preferred materials are those metals specified hereinabove for the rod member 2.

The projection 3 can have a spherical, barrelled, or cylindrical configuration. The cross-sectional configuration can be such that it will be in direct contact with the bore of the implant, as is indicated in the drawings. However, in accordance with one aspect of the invention, the projection 3 may be arranged with a clearance with respect to the bore of the implant, i.e., the diameter of the projection can be smaller than the diameter of the bore in which it is received. The clearance can be of the order of from a few $\mu m$ to a few tenth of a mm. Preferred is a play of 10 to 50 $\mu m$. In accordance with a preferred embodiment of the invention, the projection is in the form of a sphere or similar round member. The sphere is preferably provided with a central bore 3a (see FIG. 5). The diameter of the bore 3a of the sphere corresponds to the outer diameter of the rod member 2. Bore 3a preferably exhibits a circular cross section. It is also preferred that the bore 3a of the projection 3 is furnished with an internal thread, so that the projection is movably arranged on the rod member 2, which is furnished with a cooperatingly arranged external thread, whereby after the projection 3 is brought to the predetermined operating position it will be rigidly fixed on rod member 2. The operating position can also be fixed by nuts, not shown, at both ends of the rod.

A particularly preferred connecting device in accordance with the invention comprises a connecting device in which the rod member is furnished over its full length with an external thread and wherein the projection means includes a sphere which has a central bore which is furnished with internal thread, such that the sphere can be fixedly located at any desired location on the rod.

The rod 2 and the projection 3 are furnished with an enclosure or similar envelope means, designated by the reference numerals 4, 5 and 6. The envelope is made of a suitable material, which in general has a modulus of elasticity which is lower than that of the rod 2 and the implant body 1. The envelope may be assembled using different materials, which is schematically indicated in the drawing at 4, 5 and 6, whereby the individual components of the envelope can have the same modulus of elasticity as the rod 2 or the implant member 1.

Examples of such materials are synthetic materials such as, for example, polyethylene, epoxy resins, acrylic resins, silicone rubbers and similar materials, but the metals or ceramic materials mentioned in the specification above can also be used.

It is preferred that the envelope is provided in such a manner that it includes a guide cap 4 into which the rod member 2 can be introduced and which serves to assist the centered introduction of the rod 2 and maintain a predetermined distance of the rod 2 from the bottom of the implant, while simultaneously maintaining the resilient support. The guide cap 4 is preferably of a material which has a modulus of elasticity which is greater than that for the materials of the remaining components of the envelope.

In accordance with one embodiment, the envelope is exclusively comprised of the guide cap 4. In accordance with another embodiment, the guide cap 4 does not form part of the envelope and instead the bore in the implant 1 is formed in such a way that this bore is equivalent to the bore in guide cap 4. In other words, the cross section of the bore in the lower part of the implant body 1 corresponds to the cross section of the rod member 2.

Figure 10:
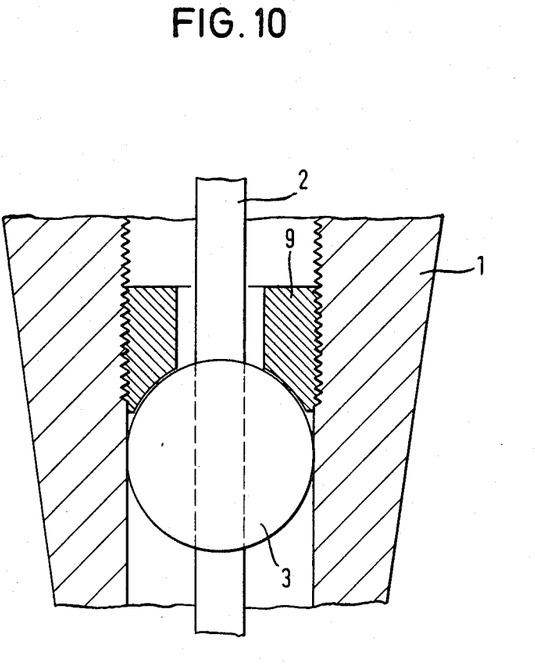
FIG. 10 is a cross section through yet another embodiment of the invention.

The envelope 4, 5 and 6 can be of any desired configuration. Thus, when viewed in cross section, it may be circular, oval, rectangular, or it may be derived from a combination of these shapes. It is preferred that the envelope has a configuration as the bore in the implant member, such that it can readily be arranged therein. The envelope can be fitted into the implant, it may be secured using a glue, or the envelope can be secured by a screw thread, or similar threaded connection, whereby the external thread of the envelope cooperates with the internal thread of the insert member 1, as is indicated in FIG. 10, showing a part 9 of the envelope.

Figure 9:
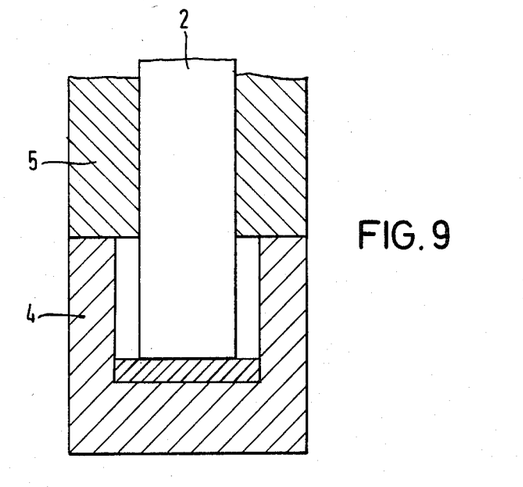
FIG. 9 is a cross section through another embodiment of the invention.

The envelope can be of the same material throughout, or it can be made of materials in which the modulus of elasticity varies. The envelope may be discontinuous to provide different deformation characteristics for different loading directions. Individual, or all, sections of the envelope can be made of one or several materials with nonlinear properties as to deformation, in order to match the mobility to the nonlinear mobility behavior of natural teeth. Between the rod member 2 and the envelope there can be provided, over certain sections, as is indicated in FIG. 9, a predetermined play, again to approximate the mobility to that of the nonlinear behavior of natural teeth.

The envelope 4, 5, 6 can be joined to the rod 2 and the projection 3 so as to be fast-secured thereto, or so as to be movable with respect thereto.

Figure 6:
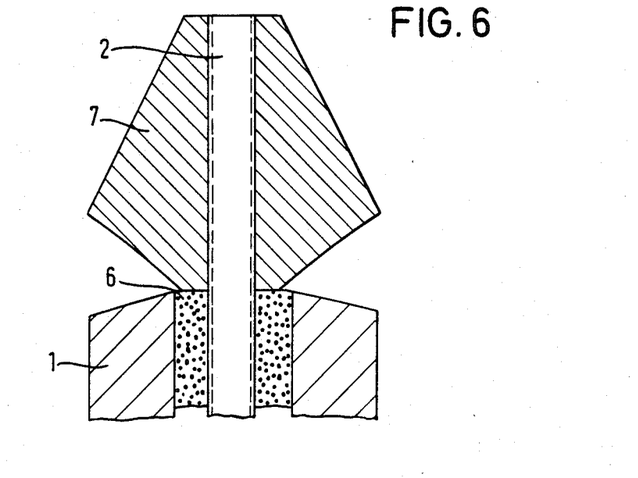
FIGS. 6, 7 and 8 show arrangements for the attachment of the superstructure.
Figure 7:
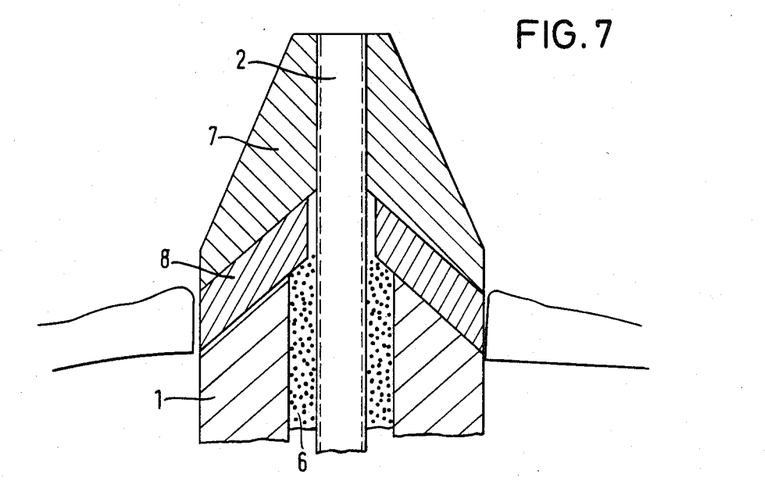
Figure 8:
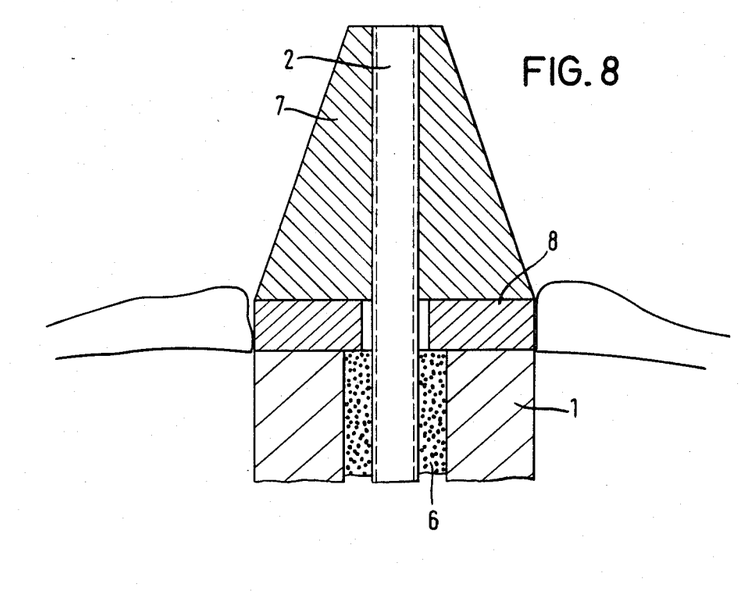

The rod member 2 is introduced together with the envelope into the implant 1 in such a manner that a part of the rod 2 extends beyond the implant. Onto this projecting part there is arranged a headpiece 7 for receiving thereon the superstructure. The headpiece can, preferably in the case of removable dentures, as is indicated in FIG. 6, be provided, on the end directed towards the implant, with a tapered or rounded depression into which the gingiva may grow. For a superstructure which is seated solidly, the headpiece 7 may have a planar end which is directed towards the implant, as is indicated in FIG. 8. Alternatively, the end directed towards the implant may include a hollow conical recess, with the angle of up to 45°, whereby in both cases the interior of the implant is protected by a correspondingly shaped seal 8. The headpiece can be secured by means of known measures to the superstructure, these being here indicated, for example, by a conical configuration.

As superstructure there can be used, in accordance with the invention, any removable or permanent dentures, or artificial joint reconstructions. It is preferred to use as superstructures, crowns, bridges or full sets of artificial teeth.

The connecting device in accordance with the present invention, in conjunction with a superstructure, which provides an ideal rigid connection to neighboring teeth, or teeth implants (for example, by a bridge), leads to a rearrangement of a horizontal force applied at the implant crown. Thereby, for one, the arising torque is compensated by the neighboring columns, leading, however, to an additional stressing of the neighboring columns, which is dependent on the dimensions of the superstructure. Furthermore, the horizontal force is distributed in equal parts to both, or respectively all columns, whereby the force component remaining for the implant is now effective from the level of the projection 3. Where the projection, preferably the sphere, is arranged in the center of rotation of the implant, there results a stress distribution as in FIG. 4, with nearly uniformly distributed low stresses in the bone base.

When using the connecting device in accordance with the invention for a single tooth replacement, there are also attained more favorable conditions as in the case of a rigid implant. As is indicated by finite-element calculations, on the basis of the characteristics of deformation of the connecting device there is also achieved a stress distribution, which leads to a reduction of the stress peaks by at least one-half in comparison with a comparable rigid implant, i.e., to conditions as they are indicated in FIG. 3. This is, for example, then the case when the part of the envelope which is located below the projection 3 has a higher modulus of elasticity than the upper part, such that a momentum is introduced for the major part into the lower part of the implant.

Reference in this disclosure to details of the specific embodiments is not intended to restrict the scope of the appended claims, which themselves recite those features regarded as essential to the invention.

We claim:

1. An endo-osseous implant adapted to connect a superstructure to the bone and to minimize stress peaks along the length of said implant thereby minimizing bone reduction or degradation, which comprises: an implant member having a bottom part adapted to be embedded in the bone, and having a bore extending therein which is closed at the bottom and open at the top, a rod having a high modulus of elasticity inserted in the bore of said implant member, said rod having a cross-sectional area smaller than that of said bore, and a length greater than that of said implant member, whereby one end thereof extends beyond the open end of said bore; means at the base of said implant member for securing the other end of said rod; projection means essentially surrounding said rod having a cross-sectional area essentially the same as the bore of said implant member, said projection means being located in said bore at a point ranging from about 0–40% of the distance from the middle of the bone embedded part of the implant member measured toward the open end of said bore; and means provided on said one end of said rod for securing a superstructure.

2. An implant according to claim 1 in which the endo-osseous implant is a dental implant and the superstructure is a denture.

3. An implant according to claim 2 in which said means for securing said rod at the base of said implant member is said bore which at the implant member base has a cross-sectional area and a shape essentially the same as that of said end of said rod.

4. An implant according to claim 2 in which said means for securing said rod at the base of said implant member is an envelope surrounding said rod end.

5. An implant according to claim 4 in which the remainder of said rod in said implant member is also surrounded by an envelope having a lower modulus of elasticity than the envelope surrounding the rod end.

6. An implant according to claim 5 in which said projection means has a circular cross section.

7. An implant according to claim 6 in which said projection means is provided with a centrally threaded bore which cooperates with threads on said rod.

8. An implant according to claim 7 in which means are threaded on to said rod to secure said projection means to said rod at either side of said projection.

9. An implant according to claim 5 in which the modulus of elasticity of said envelope surrounding the remainder of said rod is constant.

10. An implant according to claim 5 in which the modulus of elasticity of said envelope surrounding the remainder of said rod varies.

11. An implant according to claim 10 in which said envelope surrounding the remainder of said rod is discontinuous.

12. An implant according to claim 2 in which said rod has a constant cross-sectional area along the length of said implant member.

13. An implant according to claim 2 in which said rod varies in cross-sectional area along the length of said implant member.

14. An implant according to claim 2 in which the modulus of elasticity of said rod is constant along its length.

15. An implant according to claim 2 in which the modulus of elasticity of said rod varies along its length.

* * * * *